(12) United States Patent
Begg et al.

(10) Patent No.: US 11,844,857 B2
(45) Date of Patent: Dec. 19, 2023

(54) TREATING GYNECOLOGICAL MALIGNANCIES WITH DEPLOYABLE IMPLANTS

(71) Applicant: Covidien LP, Mansfield, MA (US)

(72) Inventors: Nikolai D. Begg, Wellesley, MA (US); Chad A. Pickering, Woburn, MA (US); Jordan A. Whisler, Brookline, MA (US); Rebecca D. White, Kennett Square, PA (US)

(73) Assignee: Covidien LP, Mansfield, MA (US)

( * ) Notice: Subject to any disclaimer, the term of this patent is extended or adjusted under 35 U.S.C. 154(b) by 554 days.

(21) Appl. No.: 16/875,356

(22) Filed: May 15, 2020

(65) Prior Publication Data

US 2020/0405633 A1    Dec. 31, 2020

Related U.S. Application Data

(60) Provisional application No. 62/867,581, filed on Jun. 27, 2019.

(51) Int. Cl.
| | | |
|---|---|---|
| A61F 6/16 | (2006.01) | |
| A61F 6/18 | (2006.01) | |
| A61K 9/00 | (2006.01) | |
| A61B 17/42 | (2006.01) | |
| A61K 45/06 | (2006.01) | |

(52) U.S. Cl.
CPC ............ *A61K 9/0039* (2013.01); *A61B 17/42* (2013.01); *A61F 6/16* (2013.01); *A61F 6/18* (2013.01); *A61B 2017/4216* (2013.01); *A61K 45/06* (2013.01)

(58) Field of Classification Search
CPC ............ A61B 2017/4216; A61B 17/42; A61K 9/0039; A61F 6/18; A61F 6/16; A61F 6/146; A61F 6/08; A61F 6/20; A61F 6/14; Y10S 604/904; A61M 31/00; A61M 2025/105
See application file for complete search history.

(56) References Cited

U.S. PATENT DOCUMENTS

| | | | |
|---|---|---|---|
| 3,948,259 A | | 4/1976 | Bolduc et al. |
| 4,182,328 A | * | 1/1980 | Bolduc .................. A61F 6/225 604/920 |
| 5,931,774 A | * | 8/1999 | Williams ............. A61N 5/1001 600/2 |
| 8,048,101 B2 | | 11/2011 | Lee-Sepsick et al. |
| 8,828,023 B2 | | 9/2014 | Neff et al. |
| 8,962,011 B2 | | 2/2015 | Raspagliesi |
| 9,180,039 B2 | | 11/2015 | Tal et al. |
| 9,510,088 B2 | | 11/2016 | Tal et al. |

(Continued)

FOREIGN PATENT DOCUMENTS

WO    2016025132 A1    2/2016

*Primary Examiner* — Ophelia A Hawthorne
(74) *Attorney, Agent, or Firm* — Carter, DeLuca & Farrell LLP

(57) ABSTRACT

A method of treating a gynecological malignancy includes introducing an implant within a uterus of a patient and positioning the implant adjacent to an endometrium of the uterus to enable a bioactive agent supported on the implant to treat the gynecological malignancy. The implant may be one or more deployable implants including a balloon, an IUD, a stent, or combinations thereof. Such implants may be introduced by one or more surgical instruments.

17 Claims, 7 Drawing Sheets

(56) References Cited

U.S. PATENT DOCUMENTS

| | | |
|---|---|---|
| 9,949,869 B2 | 4/2018 | Tjader et al. |
| 9,993,625 B2 * | 6/2018 | Roth .................... A61M 25/10 |
| 2011/0056501 A1 | 3/2011 | Kortesuo et al. |
| 2015/0230971 A1 | 8/2015 | Wildemeersch |

* cited by examiner

TREATING GYNECOLOGICAL MALIGNANCIES WITH DEPLOYABLE IMPLANTS

CROSS REFERENCE TO RELATED APPLICATIONS

This application claims the benefit of U.S. Provisional Application Ser. No. 62/867,581, filed Jun. 27, 2019, the entire contents of which are incorporated by reference herein.

TECHNICAL FIELD

This disclosure relates generally to deployable implants, and in particular, to deployable implants for treating gynecological malignancies such as endometrial cancer and hyperplasia.

BACKGROUND

Endometrial cancer is the most common gynecologic malignancy. It is the fourth most common cancer in women in the United States after breast, lung, and colorectal cancers. Endometrial hyperplasia is characterized by a thickening of the endometrium that is more than the typical pre- and post-menstrual buildup of endometrial tissue. Low- to medium-risk endometrial hyperplasia can be treated with nonsurgical options. The mainstay of treatment for endometrial cancer and atypical endometrial hyperplasia is a total hysterectomy. Radiation and chemotherapy can also play a role in treatment.

SUMMARY

According to one aspect, this disclosure is directed to an implant system for treating a gynecological malignancy. The system includes a surgical instrument and an implant supported by the surgical instrument. The implant is configured to be separable from the surgical instrument to maintain the implant positioned within a uterus of a patient separate from the surgical instrument. The implant includes a bioactive agent. The implant is movable between a first position and a second position, wherein in the first position, the implant is configured to be introduced into the uterus, and in a second position, the implant is configured to enable the bioactive agent to be administered from the implant to an endometrium of the uterus so that the bioactive agent treats the gynecological malignancy.

In embodiments, the bioactive agent may include a chemotherapeutic agent.

In certain embodiments, the bioactive agent may include a hormonal agent.

In various embodiments, the implant may include a bioresorbable material.

In embodiments, the implant may be semi-permeable.

In various embodiments, the implant may be configured to conform to a uterine cavity of the uterus.

In certain embodiments, the implant may be a balloon.

In some embodiments, the implant may be a stent.

In embodiments, the implant may be an IUD.

In various embodiments, the implant may include an outer surface and an inner surface. The bioactive agent may be supported on the outer surface, the inner surface, or combinations thereof.

According to one aspect, this disclosure is directed to a method of treating a gynecological malignancy. The method includes introducing an implant within a uterus of a patient utilizing a surgical instrument, positioning the implant adjacent to an endometrium of the uterus to enable a bioactive agent supported on the implant to treat the gynecological malignancy, and separating the implant from the surgical instrument so the surgical instrument can be removed from the patient when the implant is maintained within the uterus.

In some aspects, introducing the implant within the uterus of the patient utilizing the surgical instrument may include transcervically introducing the implant into the uterus.

In various aspects, positioning the implant adjacent to the endometrium of the uterus to enable the bioactive agent supported by the implant to treat the gynecological malignancy may include treating the gynecological malignancy with a chemotherapeutic agent.

In aspects, positioning the implant adjacent to the endometrium of the uterus to enable the bioactive agent supported by the implant to treat the gynecological malignancy may include treating the gynecological malignancy with a hormonal agent.

In certain aspects, treating the gynecological malignancy with the chemotherapeutic agent may include treating endometrial cancer, endometrial hyperplasia, endometriosis, or combinations thereof.

In some aspects, treating the gynecological malignancy with the hormonal agent ma include treating endometrial cancer, endometrial hyperplasia, endometriosis, or combinations thereof.

In various aspects, positioning the implant adjacent to the endometrium of the uterus to enable the bioactive agent supported by the implant to treat the gynecological malignancy may include inflating the implant with an inflation fluid to conform the implant to a uterine cavity of the uterus of the patient.

In certain aspects, introducing the implant within the uterus of the patient utilizing the surgical instrument may include introducing at least one balloon within the uterus.

In aspects, introducing the implant within the uterus of the patient utilizing the surgical instrument may include introducing at least one IUD within the uterus.

In some aspects, introducing the implant within the uterus of the patient utilizing the surgical instrument may include introducing at least one stent within the uterus.

According to yet another aspect, this disclosure is directed to a method of treating a gynecological malignancy. The method includes introducing a balloon into a uterus of a patient in an uninflated position with a surgical instrument, inflating the balloon within the uterus to an inflated position, enabling the balloon to administer bioactive agent from the balloon to an endometrium of the uterus to treat the gynecological malignancy, and maintaining the balloon within the uterus after the surgical instrument is separated from the implant and removed from the patient.

In certain aspects, the method may further comprise enabling the bioactive agent to permeate through the balloon to the endometrium of the uterus.

In some aspects, inflating the balloon within the uterus to the inflated position may include positioning an outer surface of the balloon into contact with the endometrium. Positioning the outer surface of the balloon into contact with the endometrium may include positioning the bioactive agent on an outer surface of the balloon to facilitate contact with the endometrium.

In aspects, inflating the balloon within the uterus to the inflated position may include inflating the balloon with a chemotherapeutic agent. The method may further comprise enabling the chemotherapeutic agent to permeate through the balloon.

In various aspects, inflating the balloon within the uterus to the inflated position may include inflating the balloon with a hormonal agent. The method may further comprise enabling the hormonal agent to permeate through the balloon.

In certain aspects, inflating the balloon within the uterus to the inflated position may include introducing inflation fluid through the surgical instrument and into the balloon to inflate the balloon.

In some aspects, inflating the balloon within the uterus to the inflated position may include conforming a shape of the balloon to a shape of a uterine cavity of the uterus.

According to still another aspect, this disclosure is directed to a method for treating a gynecological malignancy. The method includes positioning an IUD including a bioactive agent within a uterus, and enabling the IUD to administer the bioactive agent to an endometrium of the uterus to treat the gynecological malignancy.

According to one aspect, this disclosure is directed to a method for treating a gynecological malignancy. The method including positioning a stent including a bioactive agent within a uterus, and enabling the stent to administer the bioactive agent to an endometrium of the uterus to treat the gynecological malignancy.

According to still another aspect, this disclosure is directed to a method of treating a gynecological malignancy. The method including introducing an implant within a uterus of a patient, and positioning the implant adjacent to an endometrium of the uterus to enable a bioactive agent supported on the implant to treat the gynecological malignancy.

The details of one or more aspects of this disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with the detailed description of the embodiments given below, serve to explain the principles of the disclosure.

DETAILED DESCRIPTION

Figure 1:
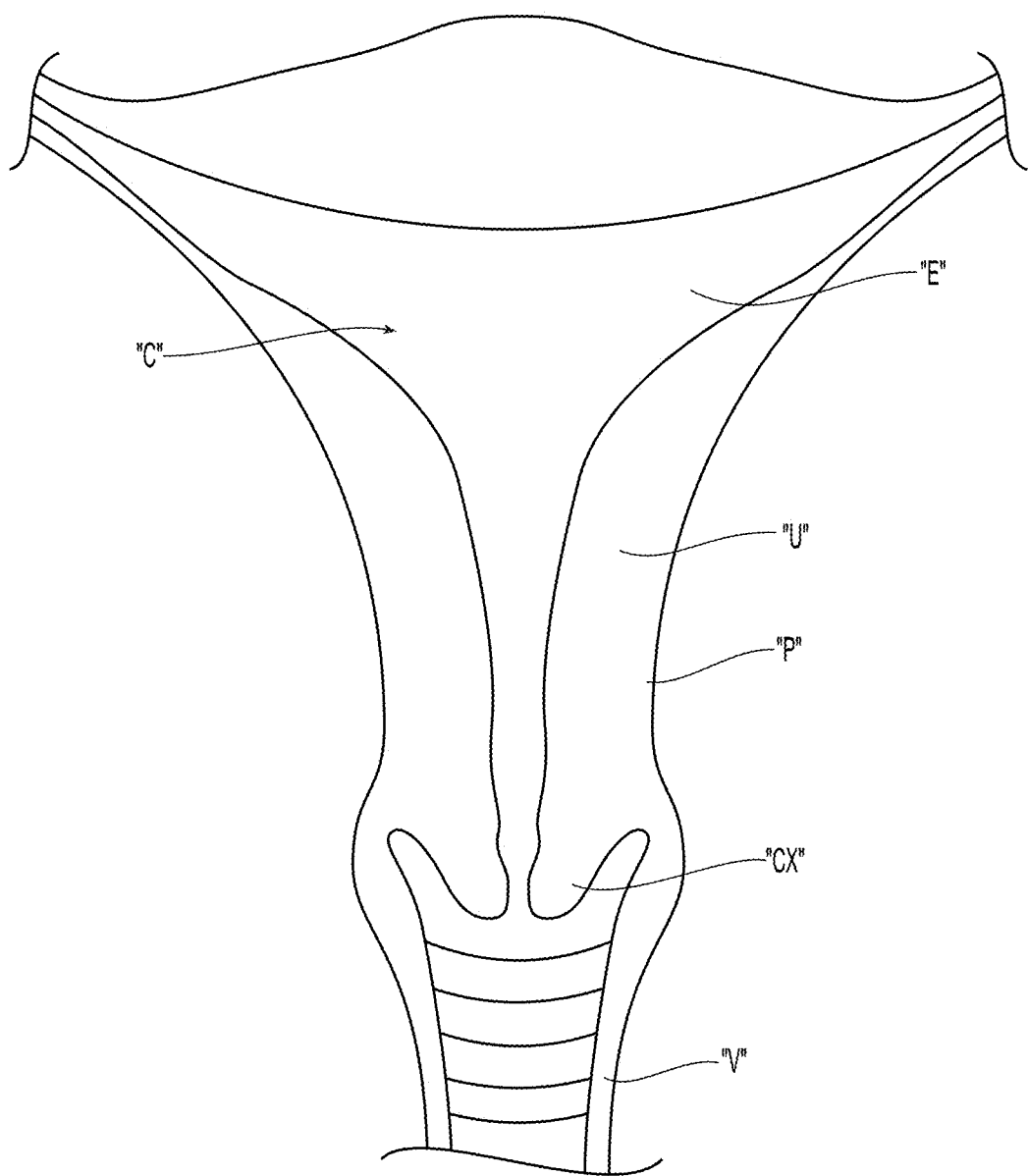
FIG. 1 illustrates portions of female reproductive anatomy.

Aspects of this disclosure are described in detail with reference to the drawings, in which like reference numerals designate identical or corresponding elements in each of the several views. Additionally, the term "proximal" refers to the portion of structure that is closer to the clinician and the term "distal" refers to the portion of structure that is farther from the clinician. As commonly known, the term "clinician" refers to a doctor (e.g., a surgeon), a nurse, or any other care provider and may include support personnel.

As used herein, the term "biodegradable" in reference to a material shall refer to the property of the material being able to be harmlessly absorbed by the body. In the present application, the terms "biodegradable," "bioresorbable," "bioerodable," and "bioabsorbable" are used interchangeably and are intended to mean the characteristic according to which a material decomposes, or loses structural integrity under body conditions (e.g., enzymatic degradation or hydrolysis) or are broken down (physically or chemically) under physiologic conditions in the body, such that the degradation products are excretable or absorbable by the body after a given period of time. The time period may vary, from about one hour to about several months or more, depending on the chemical nature of the material. In embodiments, the material may not be completely absorbed, provided the non-absorbed material poses no health risks and is biocompatible.

Further, the term "bioactive agent" includes "active therapeutic agent" (ATA) and can be used interchangeably. In its broadest sense, the term "bioactive agent" includes any substance or mixture of substances that have clinical use. The bioactive agents may invoke a biological action, exert a biological effect, or play a role in one or more biological processes. Consequently, bioactive agents may or may not have pharmacological activity per se, e.g., a dye, or fragrance. Alternatively, a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. The bioactive agent may be applied to the disclosed structure in any suitable form of matter, e.g., films, powders, liquids, gels and the like. The type and amount of bioactive agent(s) used will depend, among other factors, on the particular site and condition to be treated.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the disclosed implants and the surrounding tissues opposite the target tissue. In addition, anti-adhesive agents may be used to prevent adhesions from forming between the implants and packaging material thereof. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in a bioactive coating of this disclosure.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins, such as vitamin A, B-12, C, D, combinations thereof, and the like; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; anti-histamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents also include biologics and protein therapeutics, such as, viruses, bacteria, lipids, amino acids, cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons (β-IFN, α-IFN, and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

In the following description, well-known functions or constructions are not described in detail to avoid obscuring this disclosure in unnecessary detail.

With regard to FIG. 1, female reproductive anatomy of a female patient "P" generally includes a vagina "V" that connects to a uterus "U" defining a uterine cavity "C." A cervix "Cx" is disposed between the vagina "V" and the uterus "U." The uterus "U" is lined by an endometrium "E" that can be subject to a gynecologic malignancy such as endometrial cancer, endometrial hyperplasia, and/or endometriosis.

Figure 3:
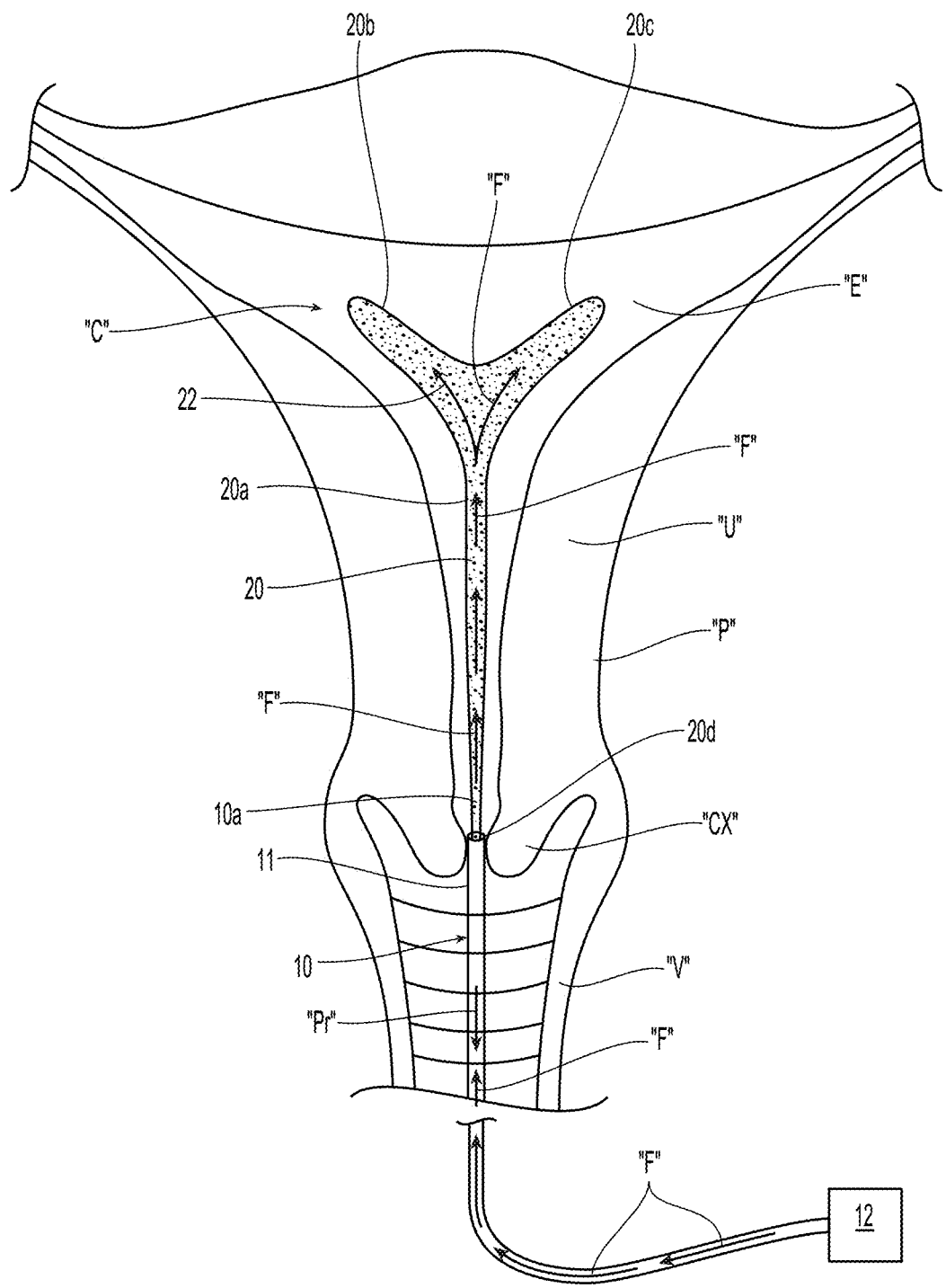
Figure 4:
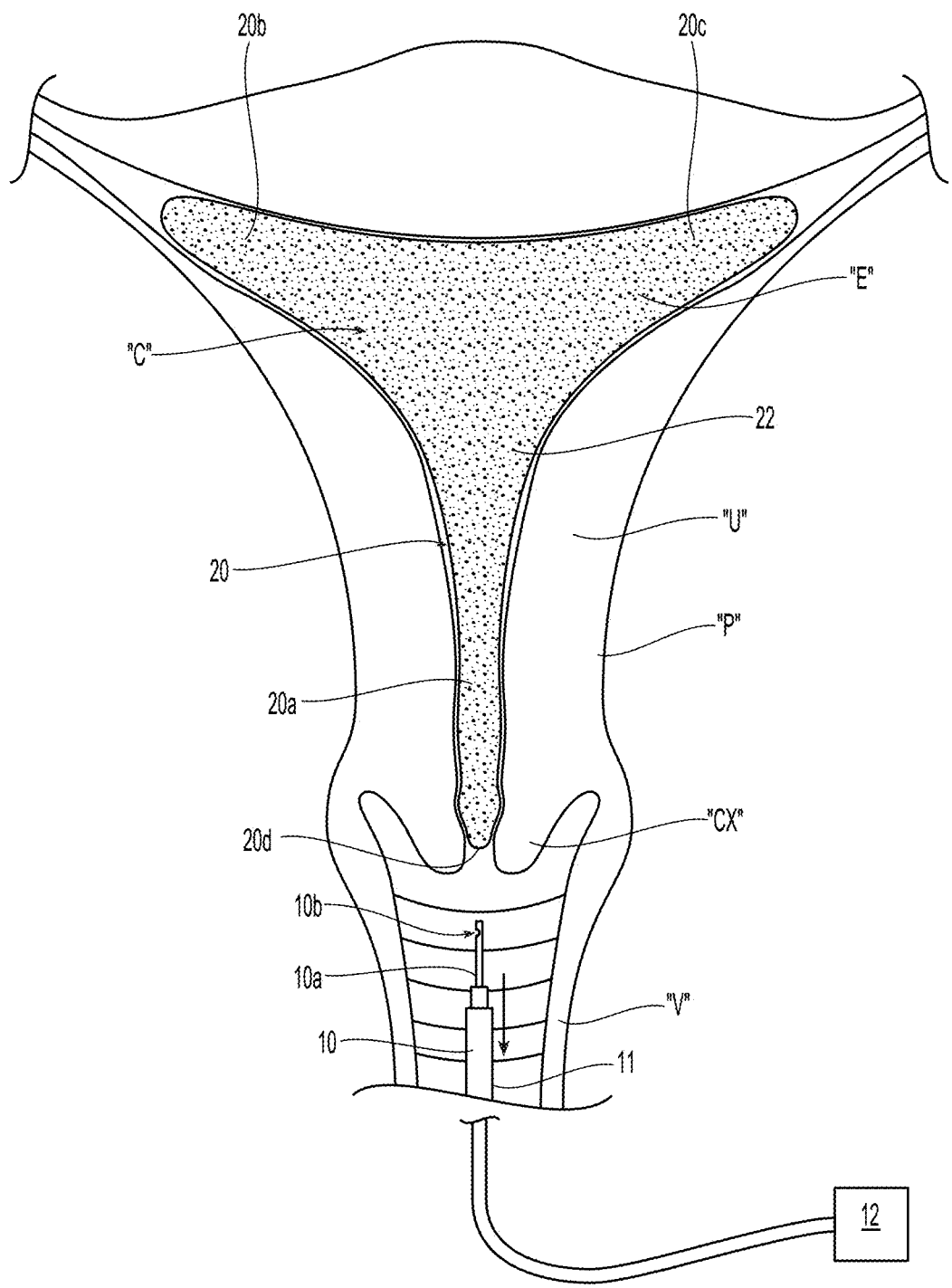
Figure 5:
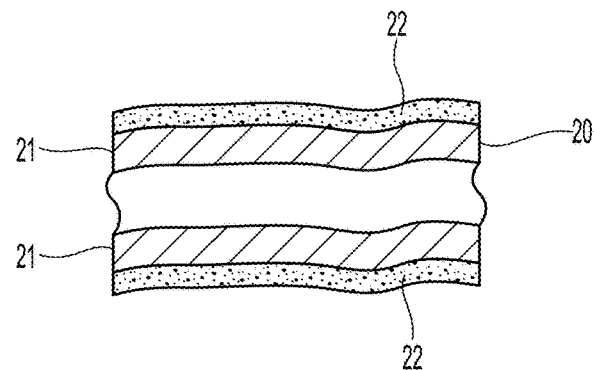
FIG. 5 is an enlarged, cross-sectional view of a portion of the deployable implant for use in the treatment of the one or more gynecological malignancies.
Figure 6A:
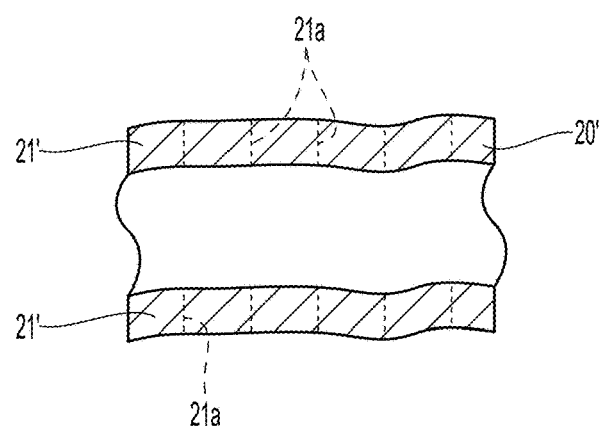
FIG. 6A is an enlarged, cross-sectional view of a portion of another embodiment of a deployable implant for use in the treatment of the one or more gynecological malignancies, the deployable implant of this embodiment shown in an uninflated position.
Figure 6B:
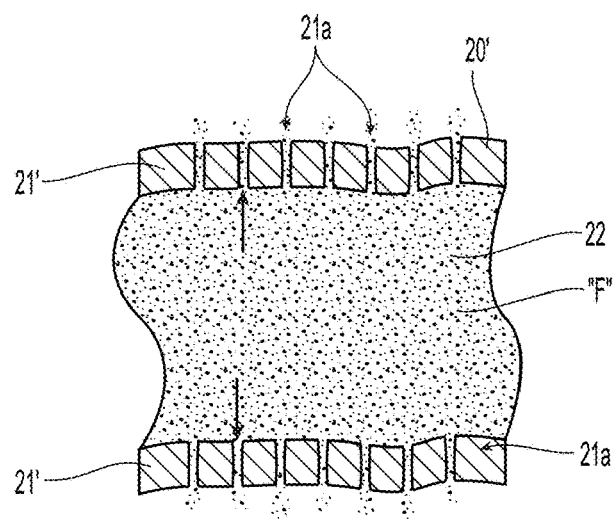
FIG. 6B is cross-sectional view of the portion of the deployable implant of FIG. 6B shown in an inflated position.

Turning to FIGS. 2-8, in order to treat such gynecologic malignancy, one or more deployable implants 20 can be introduced into the uterine cavity "C," for example, transcervically and/or transvaginally with a surgical instrument 10 configured to deploy the implants 20 into the uterus "U." Deployable implants 20 can include any suitable structure such as a balloon, an intrauterine device ("IUD"), stent, etc., or combinations thereof. Such deployable implants 20 may be self-expanding, for example, where deployable implants 20 may be flexible, may include shape memory material such as nickel-titanium alloy, or may be expandable by, for example, inflation fluid (e.g., saline). Deployable implants 20 may include any suitable biocompatible and/or biodegradable material. Deployable implants 20 can include one or more bioactive agents 22 supported on, and/or retained within, one or more inner and/or outer surfaces of deployable implants 20 (see FIG. 5 illustrating a bioactive agent 22 supported on an outer surface of implant 20). Such bioactive agents 22 can be partially and/or wholly, impregnated, layered, and/or coated on and/or in one or more surfaces of deployable implants 20.

Figure 2:
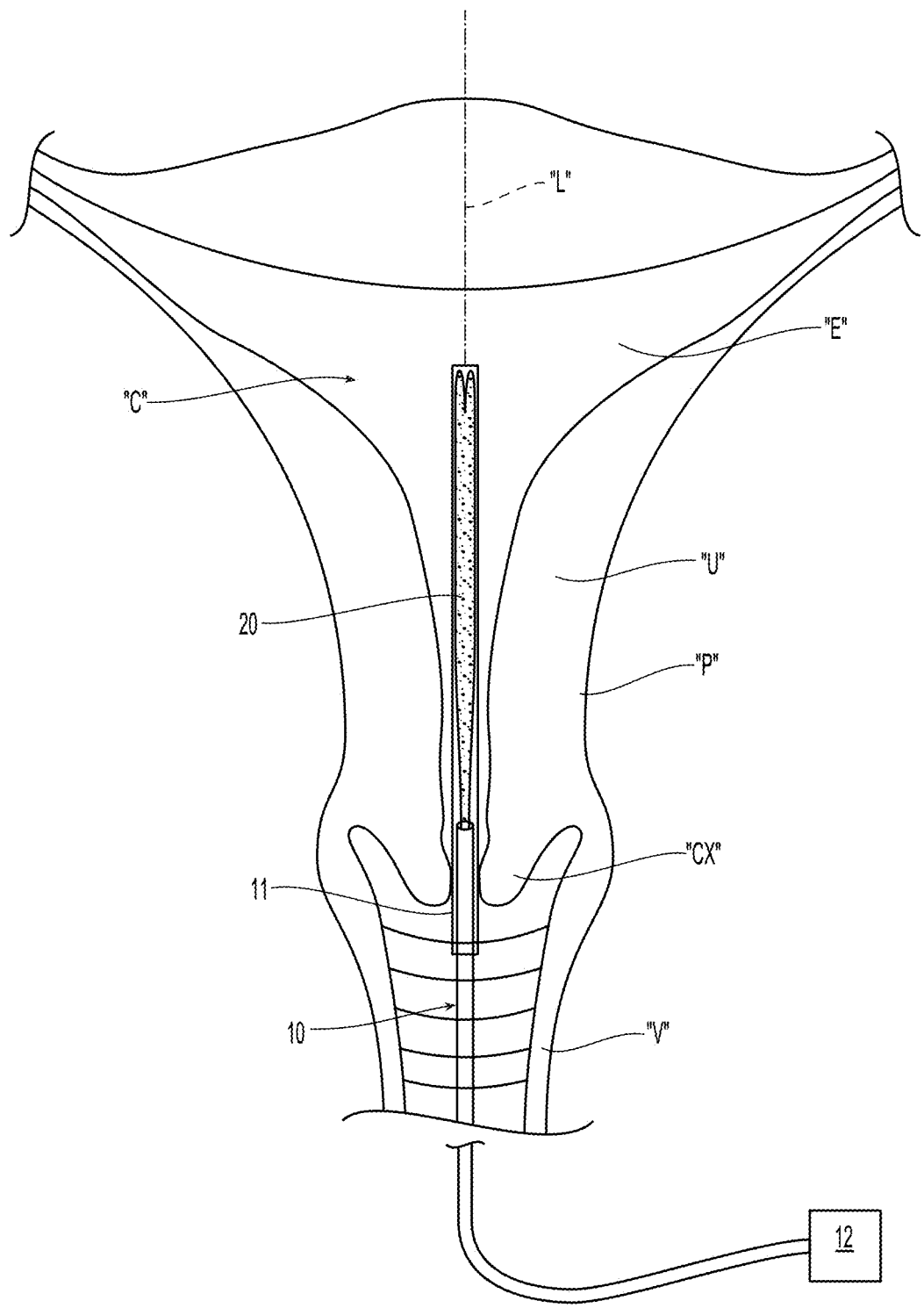
FIGS. 2-4 are progressive views illustrating treatment of one or more gynecological malignancies of the female reproductive anatomy of FIG. 1 and a deployable implant in accordance with principles of this disclosure.

With reference to FIGS. 2-4, surgical instrument 10 includes a sheath 11 that is selectively actuatable relative to surgical instrument 10 (e.g., longitudinally along axis "L" defined by surgical instrument 10 between a distal position (FIG. 2) and a proximal position (FIG. 3). Surgical instrument 10 includes an inflation needle 10a received within implant 20 to selectively inflate implant 20 within the uterus "U" of patient "P" by an inflation source 12 in fluid communication with surgical instrument 10 and implant 20. Implant 20 may be in the form of a balloon. Balloon 20 may include one or more legs 20a, 20b, 20c, and in some embodiments three legs, for instance to conform to structure of the uterine cavity "C." Balloon 20 may include an inflation port 20d (e.g., a one-way valve) to receiving inflation needle 10a of instrument 10 therein.

During insertion of balloon 20 in the uterus "U," which may be effectuated transvaginally and/or transcervically, sheath 11 of instrument 10 is disposed in the distal position thereof for supporting deployable implant 20 adjacent to instrument 10. With balloon 20 disposed in the uterine cavity "C," sheath 11 is actuated in a proximal direction, as indicated by arrow "Pr," relative to surgical instrument 10 to expose balloon 20, which may be in an uninflated position (FIG. 3) to facilitate insertion. With balloon 20 exposed and in an uninflated position, balloon 20 is inflated to an inflated position (FIG. 4), via one or more apertures 10b of inflation needle 10a of instrument 10, with inflation fluid "F" from inflation source 12. Balloon 20 may be inflated to conform to uterine cavity "C" such that outer surfaces of balloon 20 contact the endometrium "E" of uterus "U" such that bioactive agent 22 can treat a gynecological malignancy of the uterus "U." Once balloon 20 is inflated, the inflation needle 10a is removed from balloon 20 such that surgical instrument 10 can be separated or deployed from balloon 20 so that surgical instrument 10 can be removed (e.g., transvaginally) with balloon 20 maintained within uterus "U" to enable bioactive agent 22 from balloon 20 to treat the gynecological malignancy for any desired period (e.g., hours, days, weeks, months, etc.). Sheath 11 can be re-advanced to the distal position thereof to cover inflation needle 10a to facilitate safe removal of surgical instrument 10.

Surgical instrument 10 can be re-introduced into inflation port 20d to selectively deflate balloon 20 to facilitate removal of balloon 20 by surgical instrument 10 (and/or one or more other surgical instruments such as a grasper not shown), for instance, when a desired treatment period is complete.

In embodiments, implant 20' can be permeable and/or semi-permeable. For example, implant 20' includes a wall 21' defining any number of channels 21a that may be closed when implant 20' is in a first position, such as an uninflated position (FIG. 6A), and which may open when implant 20' is inflated (FIG. 6B) to enable fluid "F" (e.g., inflation fluid), which may include bioactive agent 22, to egress from implant 20' through channels 21a for treating a gynecological malignancy (e.g., endometrial cancer). In some embodiments, bioactive agent 22 may be supported within or along one or more channels 21a so that inflation fluid "F" picks up and carries bioactive agent 22 from channels 21a into uterus "U" when implant 20' inflates sufficiently to open channels 21a.

Figure 7:
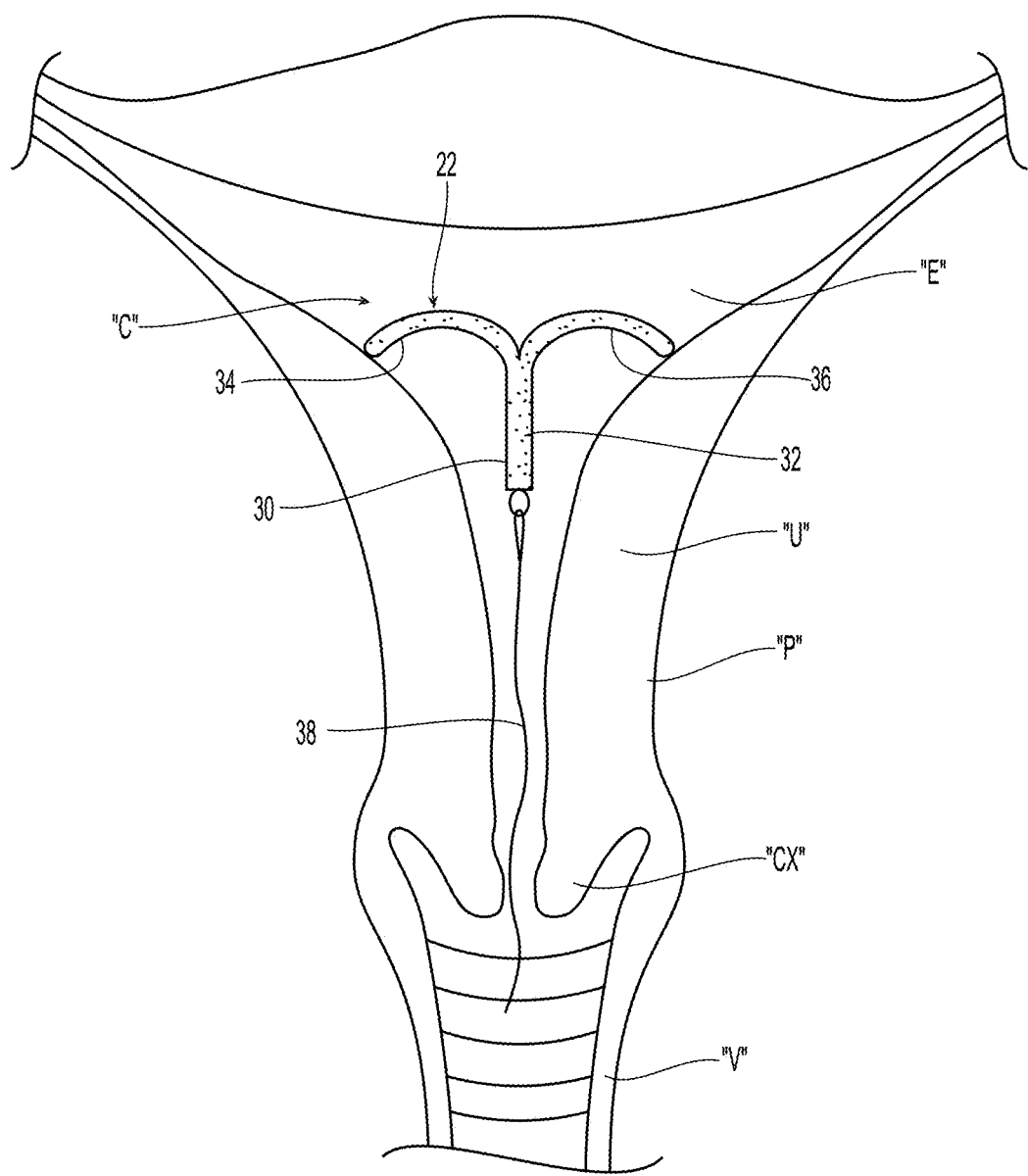
FIG. 7 is a view illustrating another embodiment of a deployable implant for use in the treatment of the one or more gynecological malignancies, the deployable implant of this embodiment shown positioned within the female reproductive anatomy of FIG. 1 in accordance with the principles of this disclosure.

With reference to FIG. 7, one embodiment of an implant of this disclosure may be in the form of an intrauterine device or IUD 30. IUD 30 includes a body portion 32 having wings 34, 36 supported on a distal end of body portion 32 for supporting IUD 30 in a uterus cavity "C" of a uterus "U." Wings 34, 36 may be flexibly attached to body portion 32 to facilitate insertion of IUD 30 in uterus cavity "C." Body portion 32 can further include a tether 38 extending from a proximal end of body portion to facilitate removal of IUD 30 from uterus cavity "C." IUD 30, like the other implants disclosed herein, supports a bioactive agent 22 to enable IUD 30 to treat a gynecological malignancy of the uterus "U."

Figure 8:
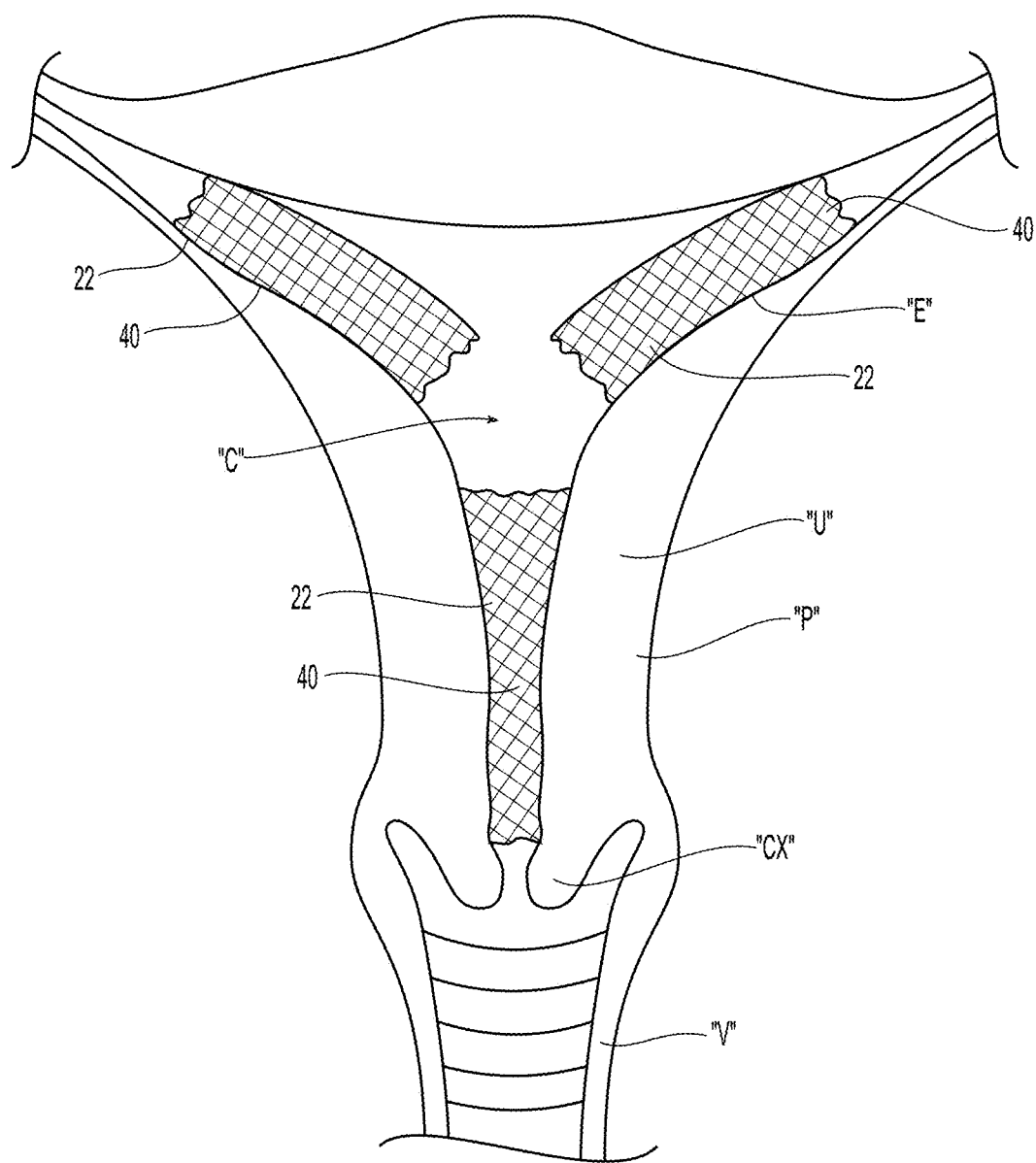
FIG. 8 is a view illustrating a number of other embodiments of deployable implants for use in the treatment of the one or more gynecological malignancies, these deployable implants shown positioned within the female reproductive anatomy of FIG. 1 in accordance with the principles of this disclosure.

In an alternative embodiment, seen in FIG. 8, for example, an implant of this disclosure may be in the form of one or more stents 40, which may be in the form of a balloon and/or self-expanding stent, and which supports bioactive agent 22 (e.g., on inner and/or outer surfaces thereof, coated, layered, impregnated, etc.) for treating a gynecological malignancy of the uterus "U." In one embodiment, stent 40 includes a plurality of branches. In some embodiments, stent 40 can be shaped to conform to a profile of the uterine cavity "C" of a uterus "U".

In some embodiments, implants may include bioresorbable or biodegradable material such as, carboxyl-methyl cellulose or CMC, for example.

The various implants disclosed herein may also be configured to be delivered by robotic surgical systems, which may include surgical instrument 10, and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, it is envisioned that the elements and features illustrated or described in connection with one exemplary embodiment may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A method of treating a gynecological malignancy, the method including:
   introducing an implant adjacent to an endometrium within a uterus of a patient utilizing a surgical instrument, the implant including:
      a bioactive agent proximate the outer surface of the implant and configured for treatment of a gynecological malignancy; and
      a plurality of channels defined within the outer surface of the implant;
   selectively expanding the implant between a first, collapsed configuration to facilitate introduction of the implant into the uterus of a patient, and a second, expanded configuration configured to force contact between an outer surface of the implant and the uterus of the patient, each channel of the plurality of channels selectively transitioning between a closed position when the implant is disposed in the first, collapsed configuration and an open position when the implant is disposed in the second, expanded configuration, wherein, upon expansion of the implant against the uterus and the opening of the channels in the second configuration, the bioactive agent is administered through the channels to the uterus; and separating the implant from the surgical instrument so the surgical instrument can be removed from the patient with the implant maintained within the uterus.

2. The method of claim 1, wherein introducing the implant adjacent to the endometrium of the uterus includes treating the gynecological malignancy with a chemotherapeutic agent.

3. The method of claim 2, wherein treating the gynecological malignancy with the chemotherapeutic agent includes treating endometrial cancer, endometrial hyperplasia, endometriosis, or combinations thereof.

4. The method of claim 1, wherein introducing the implant adjacent to the endometrium of the uterus includes treating the gynecological malignancy with a hormonal agent.

5. The method of claim 4, wherein treating the gynecological malignancy with the hormonal agent includes treating endometrial cancer, endometrial hyperplasia, endometriosis, or combinations thereof.

6. The method of claim 1, wherein introducing the implant within the uterus of the patient utilizing the surgical instrument includes transcervically introducing the implant into the uterus.

7. The method of claim 1, wherein introducing the implant adjacent to the endometrium of the uterus includes inflating the implant with an inflation fluid to conform the implant to a uterine cavity of the uterus of the patient.

8. The method of claim 1, wherein introducing the implant within the uterus of the patient utilizing the surgical instrument includes introducing at least one IUD within the uterus.

9. The method of claim 1, wherein introducing the implant within the uterus of the patient utilizing the surgical instrument includes introducing at least one stent within the uterus.

10. An implant system for treating a gynecological malignancy, the system comprising:

a surgical instrument; and an implant removably coupled to the surgical instrument, the implant selectively expandable between a first, collapsed configuration configured to facilitate introduction into a uterus of a patient, and a second, expanded configuration configured to force contact between an outer surface of the implant and the uterus, the implant including:

a bioactive agent proximate the outer surface of the implant and configured to treat a gynecological malignancy; and a plurality of channels defined within the outer surface of the implant, each of the channels selectively transitionable between a closed position when the implant is disposed in the first, collapsed configuration and an open position when the implant is disposed in the second, expanded configuration, wherein the implant is configured to expand into contact with the uterus and when the opening of the channels in the second configuration, and wherein the bioactive agent is configured to be administered through the channels to the uterus.

11. The implant system of claim 10, wherein the bioactive agent includes a chemotherapeutic agent.

12. The implant system of claim 10, wherein the bioactive agent includes a hormonal agent.

13. The implant system of claim 10, wherein at least a portion of the implant includes a bioresorbable material.

14. The implant system of claim, 10, wherein at least a portion of the implant is semi-permeable.

15. The implant system of claim 10, wherein the implant is configured to conform to a uterine cavity of the uterus when disposed in the second configuration.

16. The implant system of claim, 10, wherein the implant is a stent.

17. The implant system of claim, 10, wherein the implant is an IUD.

* * * * *